United States Patent [19]

Gerlinger et al.

[11] Patent Number: 4,802,763
[45] Date of Patent: Feb. 7, 1989

[54] MEASURING APPARATUS FOR CHARACTERIZING A SURFACE HAVING COLOR DIRECTIONAL REFLECTANCE PROPERTIES

[75] Inventors: Hermann Gerlinger, Aalen-Ebnat; Gerhard Hohberg, Aalen-Dewangen; Horst Schneider, Königsbronn, all of Fed. Rep. of Germany

[73] Assignee: Carl-Zeiss-Stiftung, Heidenheim, Fed. Rep. of Germany

[21] Appl. No.: 173,151

[22] Filed: Mar. 25, 1988

[30] Foreign Application Priority Data

Mar. 30, 1987 [DE] Fed. Rep. of Germany ... 8704679[U]

[51] Int. Cl.⁴ .......................... G01J 3/36; G01J 3/42; G01N 21/47
[52] U.S. Cl. .................................... 356/319; 356/328; 356/446
[58] Field of Search ............... 356/319, 326, 328, 446, 356/448

[56] References Cited

U.S. PATENT DOCUMENTS

| | | | |
|---|---|---|---|
| 3,806,256 | 4/1974 | Ishak | 356/446 |
| 3,999,864 | 12/1976 | Mutter | 356/448 |
| 4,479,718 | 10/1984 | Alman et al. | 356/405 |
| 4,583,858 | 4/1986 | Lebling et al. | 356/446 X |
| 4,598,715 | 7/1986 | Mächler et al. | 356/326 |
| 4,711,580 | 12/1987 | Venable | 356/446 X |
| 4,756,619 | 7/1988 | Gerlinger et al. | 356/446 X |

Primary Examiner—F. L. Evans
Attorney, Agent, or Firm—Walter Ottesen

[57] ABSTRACT

A measuring apparatus includes a freely moving measuring head which is connected to a stationary base unit via light conductors and an electrical cable. The radiation reflected from the sample is simultaneously measured at three different angles. For this purpose, three diode-array spectrometers are provided in the stationary base unit. The spectrum of the radiation illuminating the sample can be simultaneously measured with a fourth diode-array spectrometer.

13 Claims, 2 Drawing Sheets

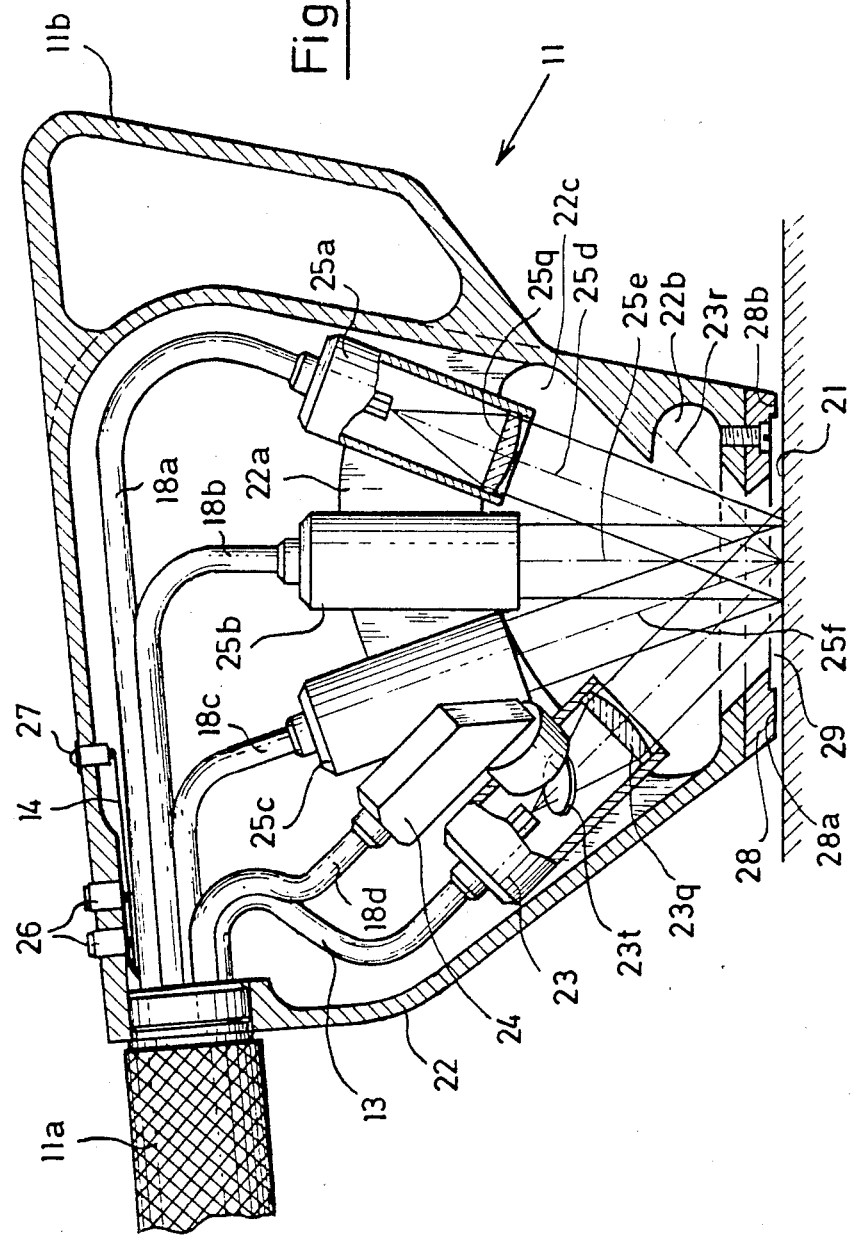

4,802,763

MEASURING APPARATUS FOR CHARACTERIZING A SURFACE HAVING COLOR DIRECTIONAL REFLECTANCE PROPERTIES

FIELD OF THE INVENTION

The invention relates to a measuring apparatus for characterizing surfaces having color directional reflectance properties. The apparatus includes a light source and several receivers.

BACKGROUND OF THE INVENTION

Surfaces having color directional reflectance properties are present, for example, in metallic paints, iridescent surfaces and in nacreous structures. In such surfaces, not only is the amount but also the spectral distribution of the reflected radiation dependent upon direction. From goniophotometric measurements on such surfaces, it is known that measurements of the reflected radiation at three different angles is required to determine a sufficient correspondence between the comparison specimen and the measured specimen.

U.S. Pat. No. 4,479,718 discloses a measuring device for measuring paint containing metallic flakes wherein a light source illuminates the surface at an angle of incidence of 45°. Three detectors are providced for detecting the reflected radiation and these detectors conjointly define respective angles of 15°, 45° and 110° with the radiatio regularly reflected at an angle of 45°.

This known measuring device has the disadvantage that the specimens to be measured have to be brought to the measuring device and must be placed adjacent a measuring opening. This is, for example, not possible in the case of an automobile chassis or structural siding.

SUMAMRY OF THE INVENTION

It is an object of the invention to provide a measuring apparatus with which large surfaces having color directional reflectance properties can also be measured.

The measuring apparatus according to the invention is for characterizing a surface having color directional reflectance properties. The measuring apparatus includes: a freely movable measuring head having a head housing; and, a stationary base unit. The stationary base unit includes a base housing; and, a light source mounted in the base housing. First light conductor means conduct light from the light source to the measuring head and light directing means mounted in the measuring head directs the light onto the surface having the directional reflectance properties. A plurality of receiving optics are arranged in the head housing for receiving the light reflected from the surface and second light conducting means conduct the reflected light to the base unit. The base unit further includes a plurality of diode-array spectrometers for receiving the reflected light from corresponding ones of said receiving optics.

An advantageous embodiment of the invention includes a beam splitter plate mounted in the measuring head so as to be disposed in the illuminating beam path of the beam illuminating the surface having the color directional reflectance properties. The radiation reflected by the beam splitter plate is conducted through a light conductor to a further diode-array spectrometer in the stationary base unit and is there received as a comparison spectrum.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
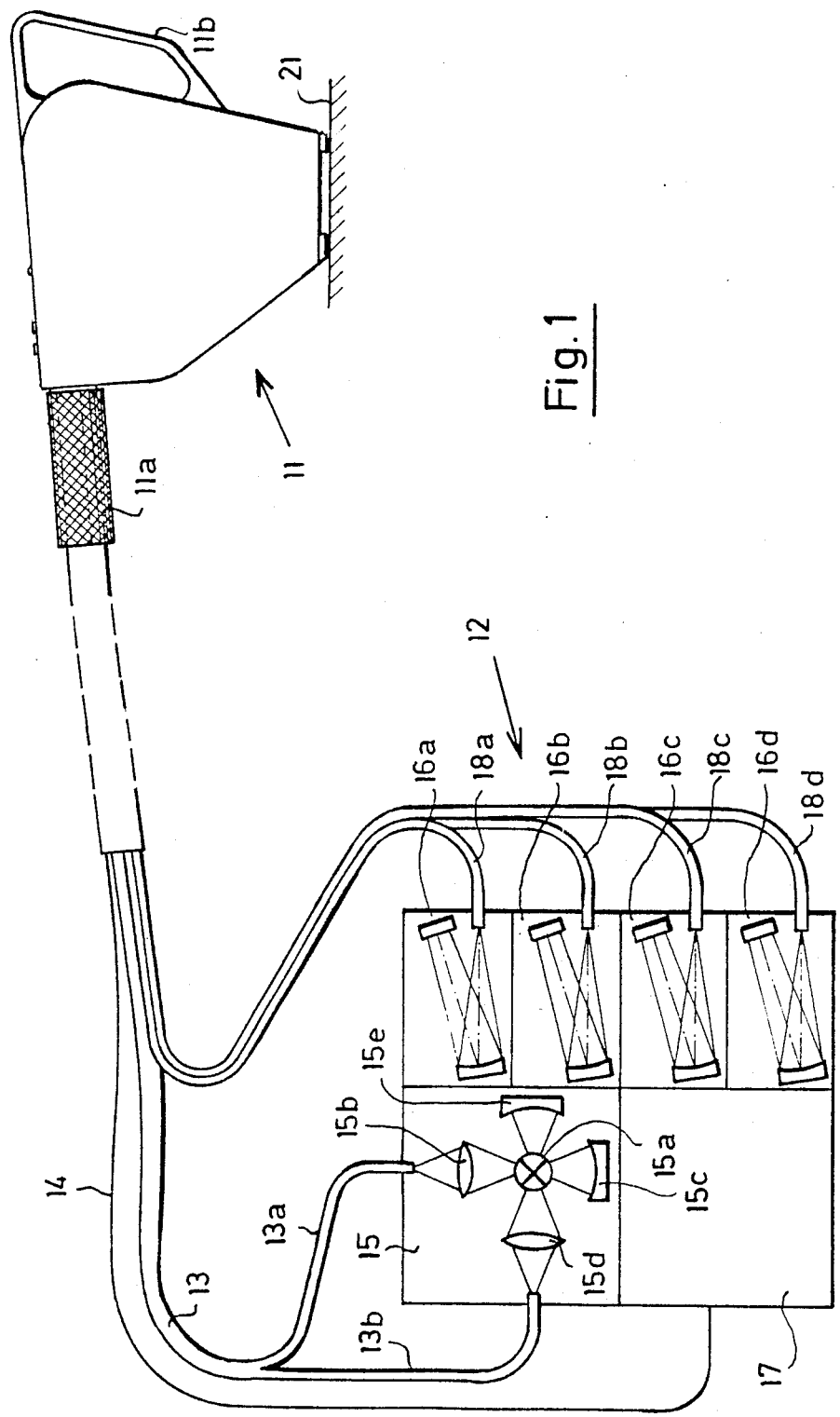
FIG. 1 is a schematic showing the configuration of the entire measuring apparatus according to the invention; and, FIG. 2 is a side elevation view, partially in section, showing details of the measuring head of the apparatus of FIG. 1.

In FIG. 1, reference numeral 11 identifies the freely movable measuring head which is connected with the stationary base unit 12 via light conductors (13, 18a to 18d) and electrical cables 14. The base unit includes a lamp housing 15 in which the light source 15a is mounted. The light source 15a is supplied with the necessary current from the electronic and evaluation unit 17.

The light source 15a is imaged onto the entrance surface of Light conductor 13a by lens 15b. The radiation flux emitted in the opposite direction is also utilized by means of the concave mirror 15c. The light source is imaged onto the entrance surface of a second light conductor 13b by means of a further lens 15d and a further concave mirror 15e which are mounted so as to be displaced by 90°. The second light conductor 13b is united with the light conductor 13a to conjointly define a common light conductor 13. In this way, not only is a doubled amount of radiation flux of the light source 15a utilized, but the illumination of the surface is relatively independent of the migrations of the focal spot of the light source 15a when the light conductors (13a and 13b) are made up of a plurality of individual fibers which are so well intermingled over the length of the common light conductor 13 that a statistical distribution of the individual fibers is present in the measuring head 11.

The measuring head 11 has a cylindrically-shaped handle 11a through which the light conductors (13, 18a to 18d) and the electrical cables 14 are guided. In addition, the measuring head 11 has a closed handle 11b by means of which it can be hung up on a hook-like suspending device at the work location. The measuring head 11 is easily manipulated and set down on the surface 21 and precisely held during the measurement with the aid of the two handles (11a and 11b).

FIG. 2 is partially in section and shows details of the measuring head 11. Measuring head 11 includes a frame-like chassis 22 with a mounting ring 22a on which the illuminating arrangement 23 and the receiving optics (25a, 25b, 25c) are attached. The measuring head is closed off by means of two plate-like formations (not shown) disposed in front of and behind as well as parallel to the plane of the drawing.

In the illuminating arrangement 23, the end surface of the light conductor 13 is arranged in the focal point of the lens 23q so that the surface 21 is illuminated by a beam having approximately parallel rays. A beam splitter plate 23t is located ahead of lens 23q and a portion of the illuminating radiation is reflected into the comparison beam receiver 24 by the beam splitter plate 23t. The comparison beam receiver 24 includes a path-folding prism (not shown) and a lens (not shown) which concentrate the comparison beam onto the inlet surface (not shown) of the light conductor 18d. The light conductor 18d leads in the stationay base unit 12 to a diode-array spectrometer 14d for receiving the comparison spectrum, that is, the spectrum of the radiation with which the surfaces 21 is charged.

The radiation regularly reflected from the surface 21 in the direction 23r is received by the light traps (22b and 22c) in the chassis 22 because this directly reflected radiation could affect the measurement. The receiving optics (25a, 25b and 25c) are provided to receive the reflected radiation and have respective axes (25d, 25e and 25f) which define the angles of, for example, 25°, 45° and 70° with the direction 23r of the regularly reflected radiation.

The receiving optics (25a, 25b and 25c) are all of the same configuration and include lenses having respective focal points in the entrance surfaces of corresponding ones of the light conductors (18a, 18b and 18c). The receiving optic 25a has a portion of its enclosure broken away to show this lens 25q. These light conductors lead to the diode-array spectrometers (16a, 16b and 16c) in the stationary base unit 12. Diode-array spectrometers are disclosed, for example, in U.S. Pat. No. 4,598,715.

By considering the comparison spectrum received by the diode-array spectrometer 16d, absolute values of the reflection spectra received by the diode-array spectrometers (16a, 16b and 16c) can be detected. The evaluation is performed in the conventional manner in the electronic and evaluation unit 17.

As the light source 15a, a halogen or xenon lamp can, for example, be used with a pulsed operation of the light source being advantageous. A short arc discharge lamp is especially suitable and can, for example, be the lamp XBO 75 manufactured by Osram or a flash lamp, for example BGS 2902Z of Heimann, which makes very short measuring times possible. Both Osram and Heimann are corporations organized and doing business in the Federal Republic of Germany.

The measuring head 11 has an opening 29 which is placed on the surface 21 in order to make measurements. A part 28 having mounting surfaces (28a and 28b) made of synthetic material such as polyethylene is arranged around the opening to prevent the sample surface from being scratched. In addition, magnets can be seated in the mounting surface of the measuring head as an aid to prevent shaking or slipping of the unit during measurements of magnetic or magnetizable samples.

Two electrical buttons 26 are provided in the region of the cylindrically-shaped handle 11a of the measuring head by means of which the measurement can be initiated and the evaluation unit 17 can be advised whether the measuring head 11 is seated on a comparison sample or a sample to be measured. One or several indicating lamps 27 can provide an indication of the different operational conditions of the measuring apparatus.

It is understood that the foregoing description is that of the preferred embodiments of the invention and that various changes and modifications may be made thereto without departing from the spirit and scope of the invention as defined in the appended claims.

What is claimed is:

1. A measuring apparatus for characterizing a surface having color directional reflectance properties, the measuring apparatus comprising:
   a freely movable measuring head having a head housing;
   a stationary base unit;
   said stationary base unit including a base housing; and, a light source mounted in said base housing;
   first light conductor means for conducting light from said light source to said measuring head;
   light directing means mounted in said measuring head for directing said light onto the surface having said properties;
   a plurality of receiving optics arranged in said head housing for receiving the light reflected from said surface;
   second light conducting means for conducting the reflected light to said base unit; and,
   said base unit further including a plurality of diode-array spectrometers for receiving the reflected light from corresponding ones of said receiving optics.

2. The measuring apparatus of claim 1, comprising an electrical cable interconnecting said base unit and said measuring head, said head housing including: a cylindrically-shaped first handle for leading said electrical cable and said first and second light conductor means into said head housing; and, a bail-like second handle for permitting said measuring head to be hung on a hook-like mounting bracket.

3. The measuring apparatus of claim 1, said light directing means directing the light onto said surface in an illuminating beam defining an illuminating beam axis of which a portion is regularly reflected along a specular beam axis, said receiving optics defining respective receiver axes and being mounted in said head housing so as to cause said receiver axes to define respective angles with said specular beam axis of 25°, 45° and 70°.

4. The measuring apparatus of claim 3, comprising: a beam splitter plate mounted in said head housing and on said illuminating beam axis for splitting out a component comparison beam from said illuminating beam; a comparison beam receiver also mounted in said head housing for receiving said comparison beam; an additional diode-array spectrometer mounted in said base housing; and, third light conducting means for conducting the light of said comparison beam to said additional diode-array spectrometer.

5. The measuring apparatus of claim 1, said head housing having a base for coming into contact engagement with said surface; and, said base being made of a plastic material.

6. The measuring apparatus of claim 5, said plastic material being polyethylene.

7. The measuring apparatus of claim 3, said measuring head including light trapping means mounted in said head housing for trapping the light regularly reflected along said specular beam axis.

8. The measuring apparatus of claim 1, said light source being a halogen lamp.

9. The measuring apparatus of claim 1, said light source being a xenon lamp.

10. The measuring apparatus of claim 1, said light source being a flash lamp.

11. The measuring apparatus of claim 1, said light directing means directing the light onto said surface in an illuminating beam defining an illuminating beam axis of which a portion is regularly reflected along a specular beam axis.

12. The measuring apparatus of claim 11, comprising: a beam splitter plate mounted in said head housing and on said illuminating beam axis for splitting out a component comparison beam from said illuminating beam; a comparison beam receiver also mounted in said head housing for receiving said comparison beam; an additional diode-array spectrometer mounted in said base housing; and, third light conducting means for conducting the light of said comparison beam to said additional diode-array spectrometer.

13. The measuring apparatus of claim 11, said measuring head including light trapping means mounted in said head housing for trapping the light regularly reflected along said specular beam axis.

* * * * *